United States Patent
Hengerer et al.

(10) Patent No.: US 10,820,804 B2
(45) Date of Patent: Nov. 3, 2020

(54) MAGNETIC RESONANCE APPARATUS WITH STANDARDIZED RADIO COUPLING WITH AN EXTERNAL DEVICE

(71) Applicant: Siemens Healthcare GmbH, Erlangen (DE)

(72) Inventors: Arne Hengerer, Moehrendorf (DE); Lars Lauer, Neunkirchen (DE); Eva Rothgang, Schwaig Bei Nuernberg (DE); Rainer Schneider, Erlangen (DE); Dirk Franger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 436 days.

(21) Appl. No.: 15/950,531

(22) Filed: Apr. 11, 2018

(65) Prior Publication Data
US 2018/0289261 A1    Oct. 11, 2018

(30) Foreign Application Priority Data

Apr. 11, 2017   (EP) .................................... 17166038

(51) Int. Cl.
*A61B 5/00*   (2006.01)
*G01R 33/563*   (2006.01)
(Continued)

(52) U.S. Cl.
CPC ............ *A61B 5/002* (2013.01); *A61B 5/0051* (2013.01); *A61B 5/0402* (2013.01); *A61B 5/4836* (2013.01); *A61M 16/024* (2017.08); *A61N 7/02* (2013.01); *G01R 33/3692* (2013.01); *G01R 33/4814* (2013.01); *G01R 33/5601* (2013.01);
(Continued)

(58) Field of Classification Search
CPC .......... G01R 33/3692; G01R 33/56358; G01R 33/4814; G01R 33/5601; A61M 16/024; A61N 7/02; A61B 5/002; A61B 5/0402; A61B 5/4836; A61B 5/0051; A61B 2576/00; A61B 5/055; H04W 76/10; H04W 80/06
See application file for complete search history.

(56) References Cited

U.S. PATENT DOCUMENTS

2003/0058502 A1   3/2003  Griffiths et al.
2005/0107681 A1   5/2005  Griffiths
(Continued)

FOREIGN PATENT DOCUMENTS

DE   10 2015 200 220 A1   7/2016

OTHER PUBLICATIONS

Gomes, "A Specification and tool for the Configuration of REST Applications"; IEEE; pp. 500-505; (2009).
(Continued)

*Primary Examiner* — Joel Lamprecht
(74) *Attorney, Agent, or Firm* — Schiff Hardin LLP

(57) ABSTRACT

A magnetic resonance system that is designed to carry out an examination of an examination object, and has an RF controller, a gradient controller and an image sequence controller, which are designed to acquire MR data of a volume portion of the examination object. An arithmetic unit of the magnetic resonance system is designed to reconstruct MR images from the acquired MR data. A standardized REST-based HTTP radio interface of the magnetic resonance system is designed to establish a standardized wireless connection to at least one external device.

15 Claims, 3 Drawing Sheets

(51) Int. Cl.
   *G01R 33/48*     (2006.01)
   *G01R 33/56*     (2006.01)
   *A61B 5/0402*    (2006.01)
   *A61M 16/00*     (2006.01)
   *A61N 7/02*      (2006.01)
   *G01R 33/36*     (2006.01)
   *A61B 5/055*     (2006.01)

(52) U.S. Cl.
   CPC ........ *G01R 33/56358* (2013.01); *A61B 5/055* (2013.01); *A61B 2576/00* (2013.01)

(56) References Cited

U.S. PATENT DOCUMENTS

| | | |
|---|---|---|
| 2014/0275970 A1 | 9/2014 | Brown et al. |
| 2017/0065823 A1 | 3/2017 | Kaib et al. |
| 2017/0205484 A1 | 7/2017 | Franger et al. |

OTHER PUBLICATIONS

"Timing of Contrast Bolus"; Screenshot from May 8, 2016 web.archive.org/web/20160508184006/http://mriquestions.com/timing-the-bolus.html.

MAGNETIC RESONANCE APPARATUS WITH STANDARDIZED RADIO COUPLING WITH AN EXTERNAL DEVICE

BACKGROUND OF THE INVENTION

Field of the Invention

The present invention concerns a magnetic resonance system and an external device, with a communications link between the external device and the magnetic resonance system.

Description of the Prior Art

In addition to the MR scanner of a magnetic resonance system and accessory equipment, such as receiving coils or support aids, devices that aid or complement the MR examination process are present in an MR examination area. These external devices include, for example, contrast medium injectors or ECG equipment. These external devices are not part of the magnetic resonance system and are usually sold separately. The external devices can be connected to the magnetic resonance system by an external trigger input. The connection to the magnetic resonance system enables clocking of the activities (for example of the contrast medium injector) or recording of particular information (for example of the ECG equipment). Without this kind of communications link between (for example) the contrast medium injector and the magnetic resonance system, the contrast medium has to be administered, and the start of the MR protocol has to occur, manually at two independent consoles, with MR angiography optimized with respect to the contrast ("contrast enhanced").

According to the prior art, the external devices are connected to the magnetic resonance system by cables, if a physical connection is created at all between the external device and the magnetic resonance system. Due to the limited space in the MR room and the sometimes numerous different machines or devices, the connection via cables is often disruptive and sometimes even associated with risks (trip hazards).

SUMMARY OF THE INVENTION

An object of the present invention therefore is to address this connection problem between an external device and a magnetic resonance system.

Within the context of the present invention, a magnetic resonance system is provided, which is configured to carry out an examination of an examination object. The magnetic resonance system has an RF controller, a gradient controller and an image sequence controller, which are configured to acquire MR data from a volume of the examination object. Furthermore, a processor of the magnetic resonance system is configured to reconstruct MR images from the acquired MR data. A standardized REST-based HTTP radio interface of the magnetic resonance system is configured to establish a standardized radio connection to an external device.

A REST-based HTTP radio interface is a standardized radio interface that uses a REST ("Representational State Transfer")-based HTTP protocol, and this advantageously enables the external device to use any method for connection to the magnetic resonance system, which supports TCP/IP and HTTP. As a communications link to the external device the inventive magnetic resonance system, in addition to WLAN, WiFi, Bluetooth, supports all further types of Internet connections.

Using the REST-based HTTP radio interface there is advantageously a bidirectional and generic interface to the magnetic resonance system for each external device, and this enables any external devices to easily be connected to the magnetic resonance system via a wireless network connection. With the REST-based HTTP radio interface a request is always triggered by the external device (in other words the client side) and a response to this request returned by the magnetic resonance system to the external device.

In combination with a wireless network the REST-based HTTP radio interface therefore easily and generically enables a wireless connection of any external device to the magnetic resonance system. The REST-based HTTP radio interface advantageously also has good expandability to provide tailor-made services for particular scenarios of external devices. The present invention therefore provides a simple and quick solution to the wireless connection of external devices, wherein an existing, generic interface framework is used by the REST-based HTTP radio interface, and this provides the basis and the framework for communication between an external device and the magnetic resonance system. Due to the inventive architecture of the magnetic resonance system, the present invention therefore provides a simple expansion capability for additional services, which can be tailor-made for specific external devices (clients) and their requests.

Explicit reference should be made to the fact that the standardized radio connection between the magnetic resonance system and the external device can also be implemented by protocols or techniques, such as Protobuf ("Protocol Buffers", a data format for serialization with an interface description language), ZeroMQ ((often also called ØMQ, 0MQ or ZMQ), and this is a very high-performance asynchronous messaging library), RabbitMQ (implements a message queue protocol, which is known as "Advanced Message Queuing Protocol" (AMQP)), etc.

In particular, the magnetic resonance system is capable of creating an instruction or an item of information and then wirelessly transmitting this instruction or information to the external device via the REST-based HTTP interface as a function of acquisition of the MR data.

This embodiment enables acquisition of the MR data to be synchronized with an action of the external device (for example a contrast medium injector).

The instruction and/or the information can be sent to the external device, for example, by a protocol known as WebSocketss.

Sending WebSocketss is based on the WebSockets protocol. The WebSockets protocol is a network protocol based on TCP, with which a bidirectional connection is possible between the magnetic resonance system (as WebSockets server) and the external device. Whereas with a pure HTTP connection an item of information or instruction can only be sent from the magnetic resonance system to the external device if the external device has made a request of the magnetic resonance system in this regard, with the WebSockets protocol it is sufficient if the external device opens the radio connection to the magnetic resonance system. The magnetic resonance system can then actively use this open connection to send information and/or instructions to the external device without having to wait for a new connection of the external device for this purpose. In technical terms, with WebSockets, as with HTTP, the external device starts a request, with the difference that, following transmission of the data for establishing a connection, the underlying TCP connection remains and enables transmissions in both directions.

Furthermore, the magnetic resonance system is designed to acquire an item of information about the REST-based HTTP interface from the external device and to carry out the step of acquisition of MR data and/or the step of reconstruction of MR images as a function of this information.

In other words, the external device can transmit information (for example ECG data) to the inventive magnetic resonance system via the connection that is created once. The magnetic resonance system can then adjust acquisition of the MR data and/or the reconstruction of the MR images to the information transmitted in this way.

In the context of the present invention, a system is also provided that, in addition to the inventive magnetic resonance system described above, also has one or more external devices.

The advantages of the inventive system essentially match the advantages of the inventive magnetic resonance system, which are stated above in detail.

The external device of the inventive system can have, for example, a control processor, a radio interface, and a sensor. The radio interface is designed to establish a standardized wireless connection (for example WLAN, WiFi, Bluetooth) to the magnetic resonance system via the REST-based HTTP interface. The sensor acquires information (for example ECG data) from the examination object to be examined. The control processor is designed to transmit this information to the magnetic resonance system via the REST-based HTTP interface via the radio interface.

If the external device is for example ECG equipment, the sensor is configured to acquire ECG data of the examination object.

According to a further inventive embodiment, the external device of the inventive system has a control processor, a radio interface, and an activator. The radio interface is designed to establish a standardized wireless connection to the magnetic resonance system via the REST-based HTTP interface. The activator is designed to stimulate the examination object or administer an administration product to the examination object. According to this embodiment, the control processor is designed to control the activator as a function of an instruction, which has been received from the magnetic resonance system via the radio interface and the REST-based HTTP interface.

According to the invention, the following variants exist for the activator:

If the external device is a contrast medium injector, the activator is configured to administer a contrast medium to the examination object as the administration product.

If the external device is to be used for MR elastography, shock waves are generated with the activator as the administration product, in order to direct these shock waves onto a particular region of the examination object. In the case of MR elastography, the examined region is cyclically compressed by shock waves acting from outside (in other words from the external device), which cease while the MR data are acquired synchronously to the shock waves or activation of the activator. Using the reconstructed MR images, portions with a different elasticity can then be identified, so that, for example, benign tumors can be distinguished from malignant ones.

The activator can be configured to generate high intensity focused ultrasound (HIFU) as the administration product, in order to direct these ultrasound waves onto a region of the examination object. These high intensity focused ultrasound waves can be used for ultrasonic ablation or for ultrasonic surgery in each case under the control of MR images generated by way of the magnetic resonance system. Precise control of heating of the region irradiated with the high intensity focused ultrasound waves is often required, and this can be carried out with temperature-sensitive sequences by the magnetic resonance system or by MR thermometry.

The activator can be a ventilation machine or ventilator in order to artificially respirate the examination object during the examination by the magnetic resonance system. The administration product is thus a gas or gases for artificial respiration. Consequently, the inventive system is also capable of artificially synchronizing a scan (acquisition of MR data) with breath-hold periods of the examination object by controlling the activation means accordingly.

In all of the inventive variants described above, the activity of the activator can advantageously be synchronized with acquisition of the MR data by the magnetic resonance system by the radio connection between the external device and the magnetic resonance system.

According to a further inventive embodiment, the external device has a control processor, a radio interface and an input element. The radio interface is configured to establish a standardized wireless connection to the magnetic resonance system via the REST-based HTTP interface while the input element detects an input of an operator (for example of a doctor operating the magnetic resonance system). In this embodiment the control processor sends an item of information to the magnetic resonance system via the REST-based HTTP interface via the radio interface of the external device as a function of the input.

In this embodiment the magnetic resonance system doctor can advantageously communicate that a particular state exists by the doctor actuating the input element (for example a simple foot pedal) at the appropriate time. A corresponding external device is known as a state publisher.

The inventive system (in particular the magnetic resonance system) is capable of forwarding the input or the information dependent on the input, which is received by one of the external devices, to one of more of the other external devices. A state publisher is more or less achieved thereby. As a result, for example a first and a second of the external devices understand that the input element (for example a button) was actuated in the case of the third of the external devices.

According to a further inventive embodiment, the inventive device has a control processor, a radio interface and output unit. The radio interface is designed to establish a standardized wireless connection to the magnetic resonance system via the REST-based HTTP interface, while the output unit is designed to emit information. As such information, the controller produces an output that is emitted as a further item of information via the output unit, which information has been received from the magnetic resonance system via the radio interface of the external device via the REST-based HTTP interface.

In this embodiment any information from the magnetic resonance system can be emitted by the output unit of the external device in order, for example, to inform the doctor operating the magnetic resonance system about a particular state of the magnetic resonance system (for example the end of data acquisition).

It should be noted that the external device does not constitute a controller of the magnetic resonance system.

The external device, therefore, does not transmit any instruction to the magnetic resonance system that would then have to be carried out by the magnetic resonance system.

In particular, each of the external devices described above can be an MR compatible external device. An MR compatible device means a device that can be used without limitation of its functionality in the environment of a magnetic resonance system, even while the magnetic resonance system acquires MR data. An MR compatible external device therefore does not disrupt the magnetic resonance system during the acquisition of MR data, nor is the MR compatible external device of the magnetic resonance system disrupted by the switching of gradients and radiation of RF pulses (during acquisition of MR data).

The external device can also be configured to carry out an information service, a patient data service, an interaction service and/or an authorization service. These services can be provided by the REST-based HTTP interface of the magnetic resonance system.

Using the information service, the external device can acquire particular information from the magnetic resonance system. This information can include for example, any of a list of sequences that can be carried out by the magnetic resonance system, a current status (for example running, open, paused) of a particular or chosen sequence, and a remaining scan time of a currently running sequence.

The patient data service provides the external device with particular information, such as the name, age, body length or weight of the patient.

A message or an indication, which is emitted by the magnetic resonance system, is forwarded to the external device by the interaction service. By this message or indication, the external device can be informed about an action of the magnetic resonance system that, for example, requires the interaction of a user.

Using authorization data, which itself usually includes a license, the authorization service acquires information about which functions of the external device can be carried out by a particular operator. The authorization service can very accurately specify which function of the respective external device can be enabled by the respective user for the magnetic resonance system, so that this function can then be performed by the magnetic resonance system or information can be transmitted to the magnetic resonance system.

DESCRIPTION OF THE PREFERRED EMBODIMENTS

Figure 1:
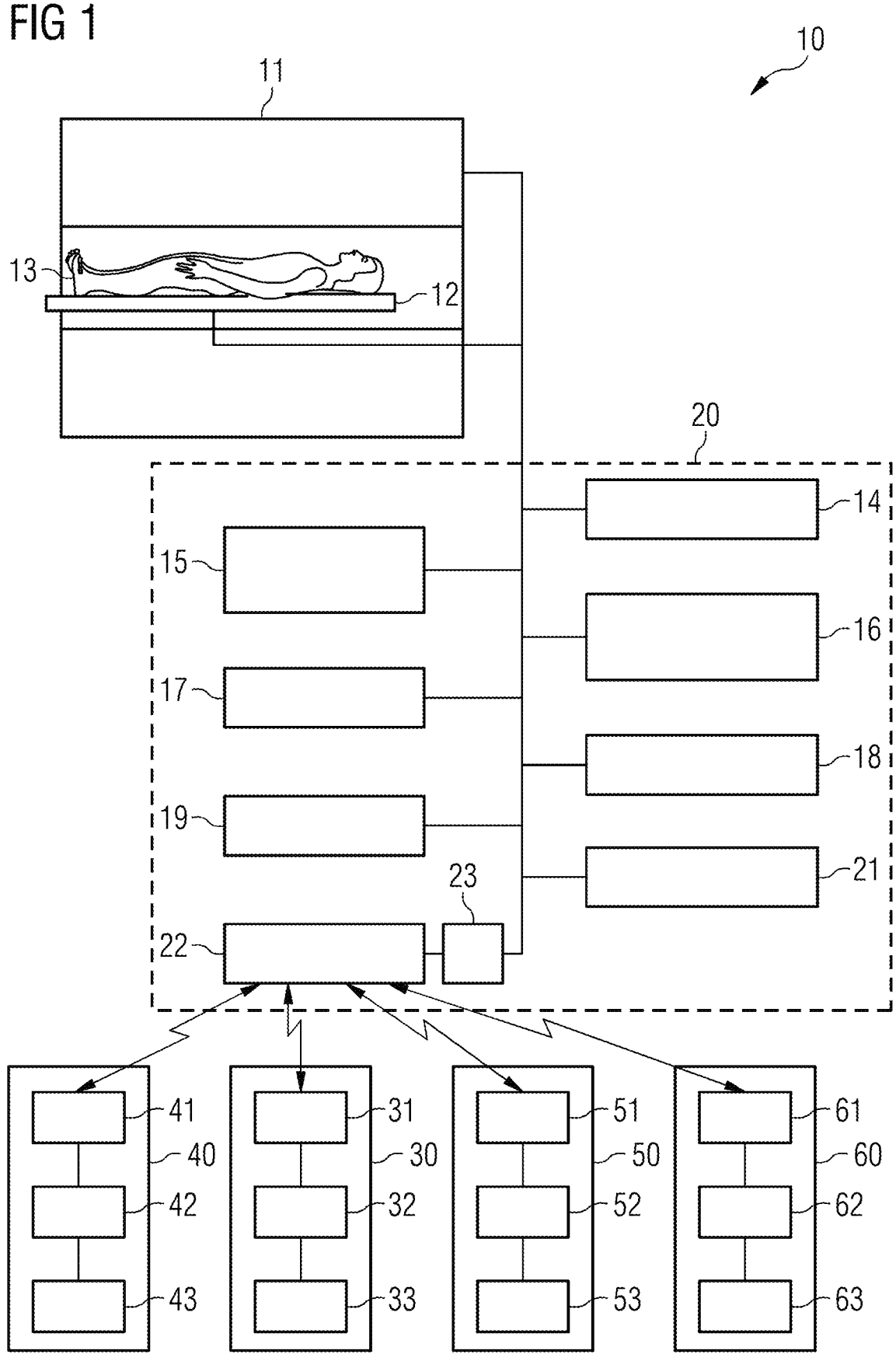
FIG. 1 schematically shows an inventive system having an inventive magnetic resonance system and four external devices.

FIG. 1 shows an inventive system that includes an inventive magnetic resonance system 10 and four external devices 30-60. The magnetic resonance system 10 has a data acquisition scanner 11 with a magnet that generates a polarization field B0. An examination person 13 arranged on a bed 12 is moved into the scanner 11 in order to record spatially encoded magnetic resonance signals from the examination person 13.

The magnetic resonance system 10 also has a control computer 20 that controls the magnetic resonance system 10. The control computer 20 has a gradient controller 15 for controlling and switching the necessary magnetic field gradients. An RF controller 14 is provided for controlling and generating the RF pulses for deflecting the magnetization. An image sequence controller 16 controls the sequence of the magnetic field gradients and RF pulses, and thereby indirectly the gradient controller 15 and the RF controller 14. An operator can operate the magnetic resonance system 10 via an input unit 17, and MR images and other information necessary for control can be displayed on a display unit 18. An arithmetic unit 19 having at least one processor (not shown) is provided for controlling the various units in the control computer 20. Furthermore, a memory 21 is provided, in which, for example, program modules or programs can be stored, which, when they are executed by the arithmetic unit 19 or its processor, control the sequence of the magnetic resonance system 10.

The magnetic resonance system 10 has a radio interface 22 and a standardized REST-based HTTP radio interface 23 to establish a standardized wireless connection to each of the external devices 30-60. The external device 30 has a radio interface 31, a control processor 32 and a sensor 33. Using the sensor means 33, the external device 30 can acquire information about the examination object 13, so that the external device 30 can be, for example, ECG equipment.

In addition to the radio interface 41 and the control processor 42, the external device 40 has an activator 43, with which the external device 40 can stimulate the examination object 13 or can administer an administration produce to the examination object 13. The external device 40 can therefore be a contrast medium injector, MR elastography equipment, a device for generating high intensity focused ultrasound or a ventilation machine.

The external device 50 also has a control processor 52 and a radio interface 51. In addition, the external device 50 has an input element 53 to acquire or detect an input of an operator, which is then transmitted to the magnetic resonance system 10 as corresponding information via the control processor 52 and the a radio interface 51.

The external device 60 has a radio interface 61, a control processor 62 and an output unit 63. The external device 60 is configured to emit an item of information via the output unit 63 with the use of the control processor 62. The external device 60 has received this information from the magnetic resonance system 10 via its radio interface 61.

The external devices 30-60 can advantageously be easily wirelessly connected to the magnetic resonance system 10 by the radio interface 22 and the REST-based HTTP radio interface 23 of the magnetic resonance system 10. Consequently, the magnetic resonance system 10 can advantageously cooperate synchronously with each of the external devices 30-60. Consequently, automatically coordinated operation between the magnetic resonance system 10 and each of the external devices 30-60 is possible with the inventive system shown in FIG. 1.

Figure 2:
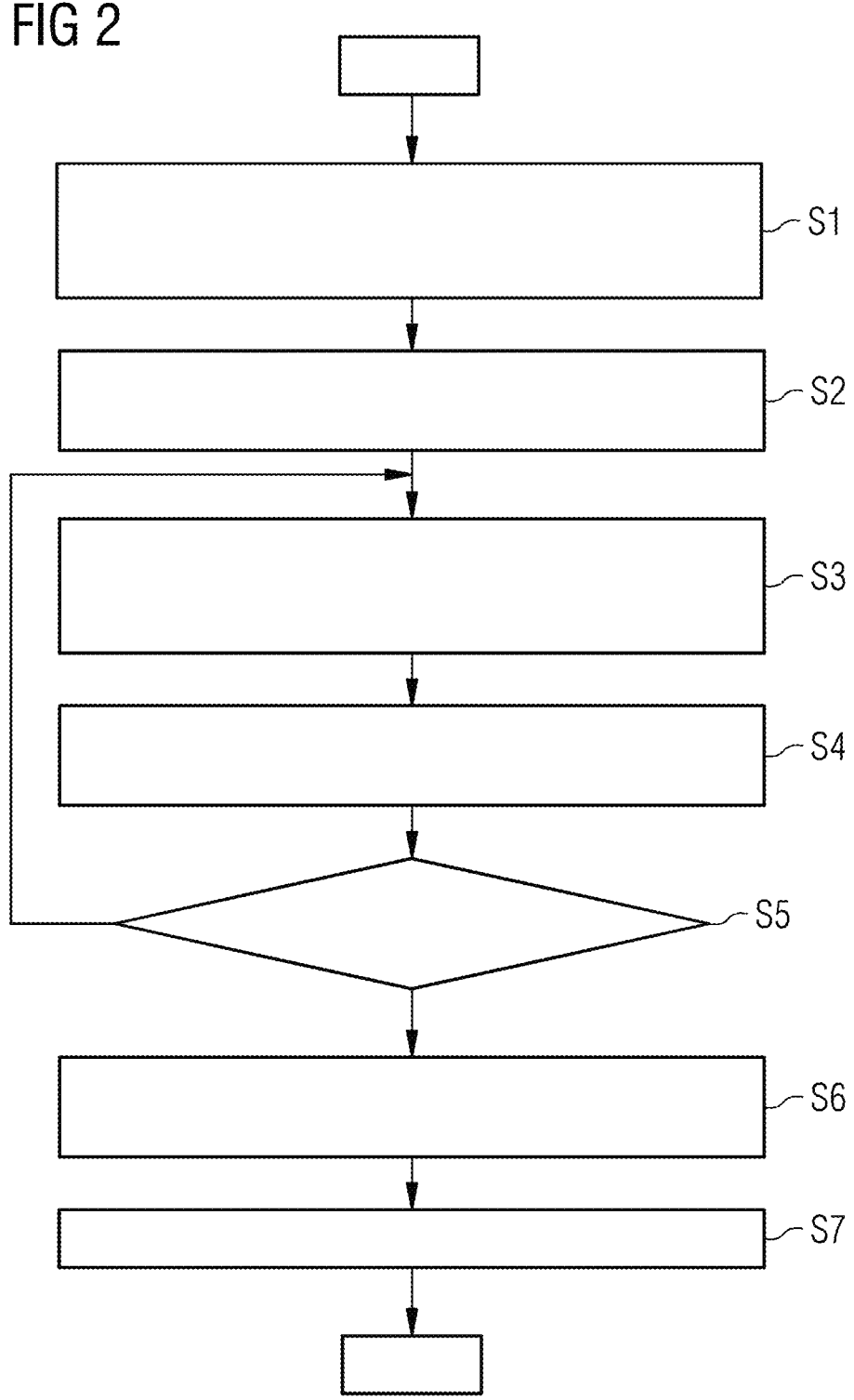
FIGS. 2 and 3 each show a flowchart to illustrate operation of an inventive system.

FIG. 2 shows the flowchart of a procedure with which operation of the inventive system shown in FIG. 1 shall be illustrated.

In step S1 an external contrast medium injector 40 is wirelessly connected to the magnetic resonance system 10 by the REST-based HTTP radio interface 23. In step S2 the magnetic resonance system 10 begins to acquire MR data from a patient 13. Coordinated with acquisition of the MR data, in step S3 the magnetic resonance system 10 automatically controls the contrast medium injector by way of WebSocketss in order to inject a contrast medium into the body of the patient 13. Even after the beginning of injection of the contrast medium, MR data of the patient continues to be acquired with the aid of the magnetic resonance system 10 in step S4. As long as there is no decision in step S5 to end injection of the contrast medium, the contrast medium continues to be injected in step S3 and MR data continues to be acquired in step S4.

Following the end of the administration of contrast medium, MR data of the patient 13 continues to be acquired in step S6 by way of the magnetic resonance system 10. Finally, MR images are reconstructed from the MR data in step S7.

Figure 3:
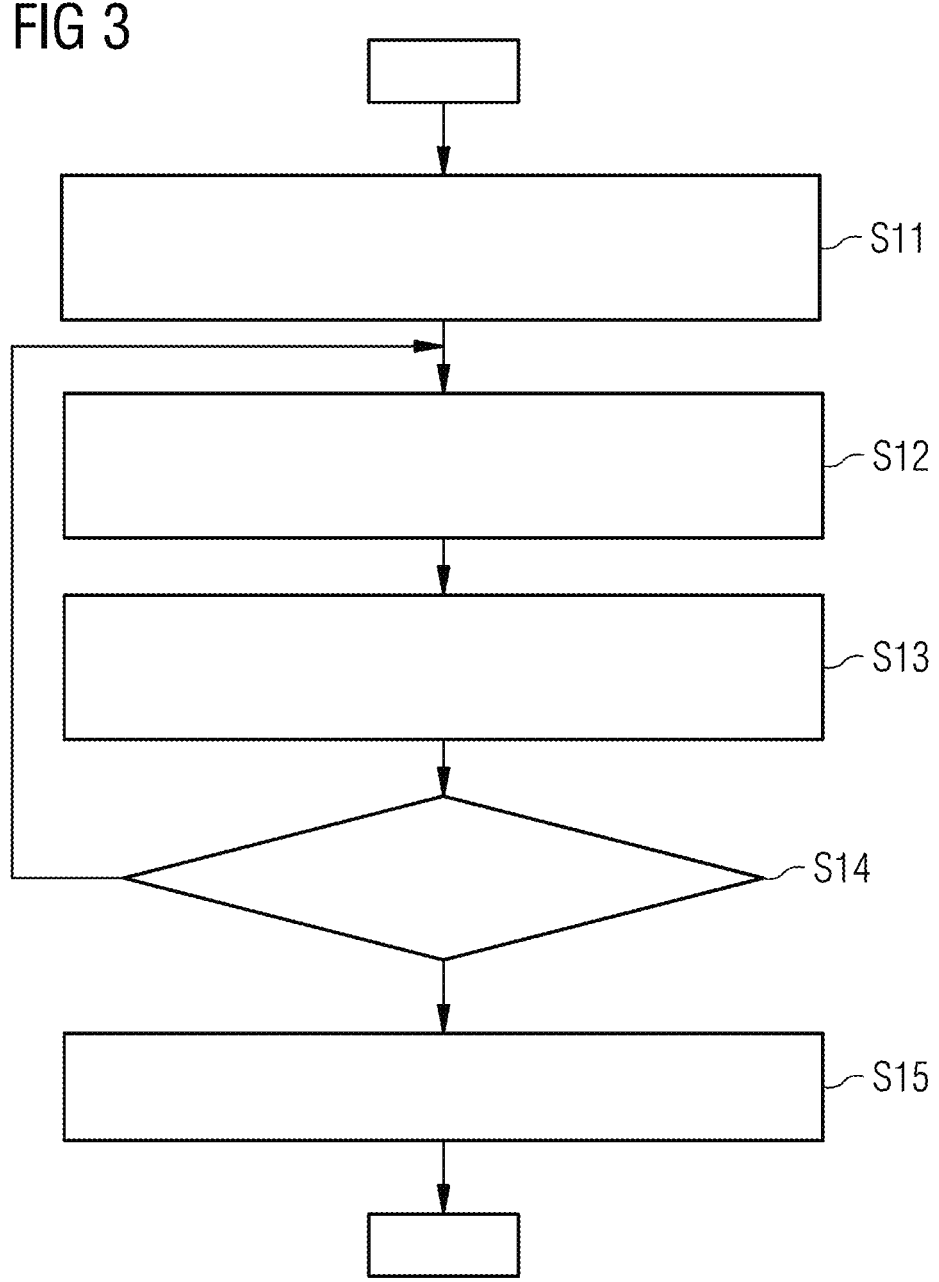

FIG. 3 shows the flowchart of a further procedure, with which a further variant of operation of the inventive system shown in FIG. 1 shall be illustrated.

In this variant external ECG equipment 30 is wirelessly connected in step S11 to the magnetic resonance system 10 by the REST-based HTTP radio interface 23. In step S12 ECG data (in other words the heartbeat) of a patient 13 is acquired using this external ECG equipment 30 and is transmitted to the magnetic resonance system 10 via the wireless communications link established in step S11. The magnetic resonance system 10 acquires this ECG data in step S13 and acquires MR data of the patient 13 as a function of the ECG data. Steps S12 and S13 are carried out repeatedly until a decision is made in step S14 to end acquisition of MR data. Finally, MR images are reconstructed from the MR data in step S15, with the acquired ECG data being taken into account.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A magnetic resonance system for carrying out an examination of an examination subject, comprising:
   an RF controller, a gradient controller, an image sequence controller configured to acquire MR data from the examination subject, and a control computer configured to collectively control the RF controller, the gradient controller, and the image sequence controller;
   an image reconstruction processor configured to reconstruct MR image data from the acquired MR data,
   wherein the control computer is configured to acquire an item of information via an interface from an external device configured to complement an MR examination process, and to carry out the acquisition of the MR or the reconstruction of the MR image data based on the information; and
   a sensor of the external device configured to acquire the information from the examination subject,
   wherein the interface is a standardized REST-based HTTP radio interface configured to establish a standardized wireless connection to the device.

2. The magnetic resonance system as claimed in claim 1, wherein the radio interface is configured to communicate the instruction or information to the external device by WebSockets.

3. A system, comprising:
   at least one external device; and
   a magnetic resonance system for carrying out an examination of an examination subject, comprising:
      an RF controller, a gradient controller, an image sequence controller configured to acquire MR data from the examination subject, and a control computer configured to collectively control the RF controller, the gradient controller, and the image sequence controller;
      an image reconstruction processor configured to reconstruct MR image data from the acquired MR data,
      wherein the control computer is configured to acquire an item of information via an interface of the at least one external device configured to complement an MR examination process, and to carry out the acquisition of the MR or the reconstruction of the MR image data based on the information, wherein the interface is a standardized REST-based HTTP radio interface configured to establish a standardized wireless connection to the at least one external device, and
   wherein the at least one external device comprises a controller, a radio, and a sensor, the sensor configured to acquire an item of information from the examination subject, the controller configured to send the information to the magnetic resonance system via the interface by the radio which is configured to establish a standardized wireless connection to the magnetic resonance system.

4. The system as claimed in claim 3, wherein the sensor is configured to acquire ECG information from the examination subject.

5. The system as claimed in claim 3, wherein the radio interface is configured to communicate the instruction or information to the external device by WebSockets.

6. A system, comprising:
   at least one external device; and
   a magnetic resonance system magnetic resonance system for carrying out an examination of an examination subject, comprising:
      an RF controller, a gradient controller, an image sequence controller configured to acquire MR data from the examination subject, and a control computer configured to collectively control the RF controller, the gradient controller, and the image sequence controller; and
      an image reconstruction processor configured to reconstruct MR image data from the acquired MR data,
      wherein the control computer is configured to generate an instruction or information based on the acquisition of the MR data by synchronizing the acquisition of the MR data with an action of the at least one external device, and to send the instruction or information to the at least one external device via an interface, wherein the at least one device is configured to aid an MR examination process, and
      wherein the interface is a standardized REST-based HTTP radio interface configured to establish a standardized wireless connection to the at least one external device, and
   wherein the at least one external device comprises a controller, a radio, and an activator, the activator configured to stimulate the examination subject or to administer a contrast medium to the examination subject, the controller configured to control the activator based on an instruction received from the magnetic resonance system via the interface by the radio which is configured to establish a standardized wireless connection to the magnetic resonance system.

7. The system as claimed in claim 6, wherein the activator is configured to administer a contrast medium to the examination subject.

8. The system as claimed in claim 6, wherein the activator is configured to generate and apply shock waves to a region of the examination subject for MR elastography.

9. The system as claimed in claim 6, wherein the activator is configured to generate high intensity, focused ultrasound (HIFU) and to apply the HIFU to a region of the examination subject.

10. The system as claimed in claim 7, wherein the activator comprises a ventilation machine to artificially respirate the examination subject.

11. The system as claimed in claim 3, wherein the at least one external device comprises an input configured to detect an input by an operator, a controller configured to send an item of information to the magnetic resonance system via the interface by the radio based on the input.

12. The system as claimed in claim 3, wherein the at least one external device comprises an output configured to output an item of information as the information, and the controller is configured to output a further item of information, which is received from the magnetic resonance system via the interface by the radio, via the output.

13. The system as claimed in claim 3, wherein the at least one external device is MR compatible.

14. The system as claimed in claim 3, wherein the at least one external device is configured to perform a device service selected from the group consisting of:
- an information service comprising presentation of a list of sequences performable by the magnetic resonance system, a current state of a particular sequence, or a remaining scan time of a sequence currently running on the magnetic resonance system,
- a patient data service comprising presentation of information about a patient serving as the examination subject,
- an interaction service configured to present an indication or a message from the magnetic resonance system, and
- an authorization service configured to determine, using authorization data, a function of the at least one external device that may be implemented by a particular operator.

15. The system as claimed in claim 6, wherein the radio interface is configured to communicate the instruction or information to the external device by WebSockets.

* * * * *